US00PP21948P2

(12) United States Plant Patent
Kanaya

(10) Patent No.: US PP21,948 P2
(45) Date of Patent: May 31, 2011

(54) ***BEGONIA* PLANT NAMED 'SUNBEGOPI'**

(50) Latin Name: *Begonia semperflorens*
Varietal Denomination: Sunbegopi

(75) Inventor: Takeshi Kanaya, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/660,953

(22) Filed: Mar. 8, 2010

(51) Int. Cl.
*A01H 5/00* (2006.01)

(52) U.S. Cl. ..... Plt./343

(58) Field of Classification Search ..... Plt./343
See application file for complete search history.

*Primary Examiner* — Annette H Para
(74) *Attorney, Agent, or Firm* — C. A. Whealy

(57) ABSTRACT

A new and distinct cultivar of *Begonia* plant named 'Sunbegopi', characterized by its upright and outwardly spreading plant habit; vigorous growth habit; freely branching habit; green-colored leaves; and numerous single pink-colored flowers that are held above and beyond the foliar plane.

1 Drawing Sheet

Botanical designation: *Begonia semperflorens*.
Cultivar denomination: 'SUNBEGOPI'.

BACKGROUND OF THE INVENTION

The present invention relates to a new and distinct cultivar of *Begonia* plant, botanically known as *Begonia semperflorens* and hereinafter referred to by the name 'Sunbegopi'.

The new *Begonia* plant is a product of a planned breeding program conducted by the Inventor in Higashiomi, Shiga, Japan. The objective of the breeding program is to create new vigorous and freely branching *Begonia* plants with an outwardly spreading plant habit and attractive leaf and flower coloration.

The new *Begonia* plant originated from a cross-pollination made by the Inventor in Higashiomi, Shiga, Japan in April, 2005 of a proprietary selection of *Begonia semperflorens* identified as code number BG58-3, not patented, as the female, or seed, parent with a proprietary selection of *Begonia semperflorens* identified as code number BG103-2, not patented, as the male, or pollen, parent. The new *Begonia* plant was discovered and selected by the Inventor as a flowering plant from within the progeny of the stated cross-pollination in a controlled environment in Higashiomi, Shiga, Japan in September, 2006.

Asexual reproduction of the new *Begonia* plant by cuttings taken in a controlled greenhouse environment in Higashiomi, Shiga, Japan since October, 2006, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunbegopi'. These characteristics in combination distinguish 'Sunbegopi' as a new and distinct *Begonia* plant:

1. Upright and outwardly spreading plant habit.
2. Vigorous growth habit.
3. Freely branching habit.
4. Green-colored leaves.
5. Numerous single pink-colored flowers that are held above and beyond the foliar plane.

Plants of the new *Begonia* differ primarily from plants of the female parent selection in flower color as plants of the female parent selection have red-colored flowers.

Plants of the new *Begonia* differ primarily from plants of the male parent selection in the following characteristics:

1. Plants of the new *Begonia* are larger than plants of the male parent selection.
2. Plants of the new *Begonia* have larger flowers than plants of the male parent selection.
3. Plants of the new *Begonia* and the male parent selection differ in flower color as plants of the male parent selection have white-colored flowers.

Plants of the new *Begonia* can be compared to plants of *Begonia* 'Baby Wing Pink', not patented. In side-by-side comparisons conducted in Higashiomi, Shiga, Japan, plants of the new *Begonia* differed primarily from plants of 'Baby Wing Pink' in the following characteristics:

1. Plants of the new *Begonia* had thicker stems than plants of 'Baby Wing Pink'.
2. Plants of the new *Begonia* had glabrous leaves whereas plants of 'Baby Wing Pink' had pubescent leaves.
3. Plants of the new *Begonia* had larger male and female flowers than plants of 'Baby Wing Pink'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph at the top of the sheet comprises a side perspective view of a typical flowering plant of 'Sunbegopi' grown in a container.

The photograph at the bottom of the sheet is a close up view of a typical plant of 'Sunbegopi'.

DETAILED BOTANICAL DESCRIPTION

The aforementioned photographs and following observations and measurements describe plants grown in 15-cm containers during the early summer in Higashiomi, Shiga, Japan, under commercial practice in an outdoor nursery. During the production of the plants, the day temperatures averaged 23° C. and the night temperatures averaged 13° C. Plants were four months old when the photographs and description were taken. In the following description, color references are made to The Royal Horticultural Society Colour Chart, 2001 Edition, except where general terms of ordinary dictionary significance are used.

Botanical classification: *Begonia semperflorens* 'Sunbegopi'.

Parentage:

*Female, or seed, parent.*—Proprietary selection of *Begonia semperflorens* identified as code number BG58-3, not patented.

*Male, or pollen, parent.*—Proprietary selection of *Begonia semperflorens* identified as code number BG103-2, not patented.

Propagation:

*Type.*—By cuttings.

*Time to initiate roots.*—About two weeks at temperatures of 20° C. to 25° C.

*Time to produce a rooted young plant.*—About 30 days at temperatures of 20° C. to 25° C.

*Root description.*—Fine, fibrous; white in color.

*Rooting habit.*—Freely branching; plants of the new *Begonia* have not been observed to form tubers.

Plant description:

*Plant form and growth habit.*—Upright and outwardly spreading habit, broad inverted triangle; freely branching with good stem strength; flowers are single and positioned above the foliar plane; vigorous growth habit.

*Plant height.*—About 23.2 cm.

*Plant width.*—About 34.2 cm.

*Lateral branches.*—Length: About 15.6 cm. Diameter: About 9.9 mm. Internode length: About 3.4 cm. Aspect: Upright to outwardly. Texture: Smooth, glabrous. Color: Close to 144A tinted with close to 60A.

*Leaves.*—Arrangement: Alternate; simple. Length: About 9.7 cm. Width: About 8.4 cm. Shape: Roughly reniform, asymmetrical. Apex: Acute to obtuse. Base: Cordate. Margin: Shallowly serrate. Texture, upper and lower surfaces: Smooth, glabrous. Venation pattern: Palmate. Color: Developing leaves, upper surface: Close to 144A; towards the margins, close to 60A. Developing leaves, lower surface: Close to 147B; towards the margins, close to 60A. Fully expanded leaves, upper surface: Close to 144A; towards the margins, close to 60B; venation, close to 145B. Fully expanded leaves, lower surface: Close to 148B; towards the margins, close to 60B; venation, close to 145B. Petioles: Length: About 3.2 cm. Diameter: About 3.2 mm. Texture, upper and lower surfaces: Smooth, glabrous. Color, upper and lower surfaces: Close to 145A tinted with close to 60B. Stipules: Length: About 2.2 cm. Width: About 1.2 cm. Shape: Ovate. Apex: Acute. Base: Truncate. Margin: Entire. Texture, upper and lower surfaces: Smooth, glabrous. Color, upper and lower surfaces: Close to 145C; towards the margins, close to 60B.

Flower description:

*Flowering habit.*—Single flowers arranged in axillary cymes; usually about two to five flowers per cyme and about 13 cymes per plant; flowers positioned above and beyond the foliar plane.

*Natural flowering season.*—Plants begin flowering about 60 days after planting; in the garden, plants flower continuously from the spring to the autumn in Japan; male flowers not persistent; female flowers persistent.

*Fragrance.*—None detected.

*Male flowers buds.*—Length: About 2.6 cm. Diameter: About 2.6 cm. Shape: Rounded. Color: Close to 58C.

*Male flowers.*—Shape: Cruciform. Diameter: About 4.2 cm. Depth (height): About 5.5 cm. Aspect: Outwardly to drooping. Tepals: Quantity: Four per flower; two larger and two smaller tepals. Length, larger tepals: About 3 cm. Length, smaller tepals: About 1.8 cm. Width, larger tepals: About 3 cm. Width, smaller tepals: About 8 mm. Shape, larger tepals: Rounded. Shape, smaller tepals: Narrowly obovate. Apex, all tepals: Rounded. Base, larger tepals: Rounded. Base, smaller tepals: Acute. Margin, all tepals: Entire. Texture, all tepals, upper and lower surfaces: Smooth, glabrous. Color, all tepals: When opening and fully opened, upper surface: Close to 63D. When opening and fully opened, lower surface: Close to 63D.

*Female flowers buds.*—Length: About 2.2 cm. Diameter: About 1.6 cm. Shape: Rounded to ovate. Color: Close to N57D.

*Female flowers.*—Shape: Rounded. Diameter: About 3.6 cm. Depth (height): About 2.5 cm. Aspect: Drooping. Tepals: Quantity: Five or six per flower in a single whorl. Length: About 1.4 cm to 2.2 cm. Width: About 5 mm to 16 mm. Shape: Obovate to narrowly obovate. Apex: Rounded. Base: Obtuse to acute. Margin: Entire. Texture, upper and lower surfaces: Smooth, glabrous. Color: When opening and fully opened, upper surface: Close to 73B to 73C. When opening and fully opened, lower surface: Close to 73B to 73C.

*Flower bracts.*—Length: About 8.5 mm. Width: About 6 nun Color: Close to 61B.

*Peduncles.*—Angle: Outwardly. Length: About 3.7 cm. Diameter: About 2 mm. Texture: Smooth, glabrous. Color: Close to 73B tinted with close to 60A.

*Pedicels.*—Angle: Outwardly to drooping. Length: About 1.7 cm. Diameter: About 1.2 mm. Texture: Smooth, glabrous. Color: Close to 73B tinted with close to 60A.

*Reproductive organs.*—Stamens: Quantity: About 79 per male flower. Length: About 7.2 mm. Anther shape: Elliptical. Anther length: About 3 mm. Anther diameter: About 1 mm. Anther color: Close to 12A. Pollen amount: Moderate. Pollen color: Close to 12B. Pistils: Quantity: One per female flower. Length: About 6.1 mm. Stigma shape: Six-lobed, convoluted. Stigma color: Close to 12A. Style color: Close to 12A. Ovary length: About 2.8 cm. Ovary diameter: About 3.1 cm. Ovary color: Close to 63B.

*Seed/fruit.*—Seed and fruit production have not been observed on plants of the new *Begonia*.

Postproduction longevity: Excellent postproduction longevity, plants last about 180 days.

Disease/pest resistance: Resistance to pathogens and pests common to *Begonias* has not been observed.

Temperature tolerance: Plants of the new *Begonia* have been observed to tolerate temperatures from about 15° C. to about 35° C.

It is claimed:

1. A new and distinct *Begonia* plant named 'Sunbegopi' as illustrated and described.

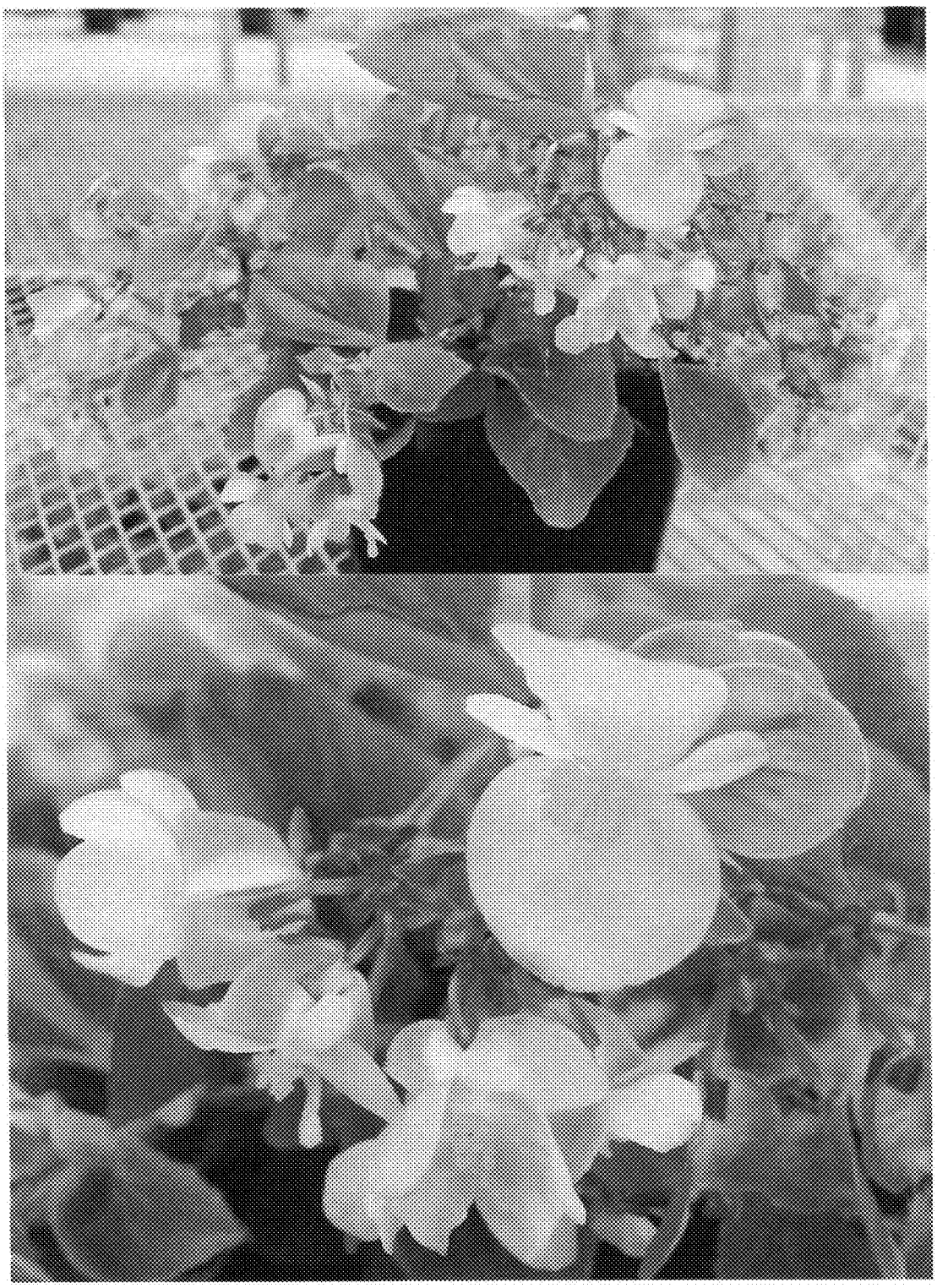

* * * * *